(12) United States Patent
Saikia et al.

(10) Patent No.: US 9,006,467 B2
(45) Date of Patent: Apr. 14, 2015

(54) 1,2,3-TRIAZOLE CONTAINING ARTEMISININ COMPOUNDS AND PROCESS FOR PREPARATION THEREOF

(75) Inventors: Bishwajit Saikia, Jorhat (IN); Nabin C. Barua, Jorhat (IN); Partha P. Saikia, Jorhat (IN); Abhishek Goswami, Jorhat (IN); Paruchuri G. Rao, Jorhat (IN); Ajit K. Saxena, Jammu (IN); Nitasha Suri, Jammu (IN)

(73) Assignee: Councel of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/985,527

(22) PCT Filed: Feb. 14, 2012

(86) PCT No.: PCT/IN2012/000099
§ 371 (c)(1),
(2), (4) Date: Aug. 14, 2013

(87) PCT Pub. No.: WO2012/111025
PCT Pub. Date: Aug. 23, 2012

(65) Prior Publication Data
US 2013/0331581 A1 Dec. 12, 2013

(30) Foreign Application Priority Data
Feb. 14, 2011 (IN) .............................. 366/DEL2011

(51) Int. Cl.
*C07D 493/18* (2006.01)

(52) U.S. Cl.
CPC ................................. *C07D 493/18* (2013.01)

(58) Field of Classification Search
USPC .......................................... 514/450; 549/346
See application file for complete search history.

(56) References Cited

FOREIGN PATENT DOCUMENTS

| | | | |
|---|---|---|---|
| CN | 1296009 | A | 5/2001 |
| WO | 9701548 | A1 | 1/1997 |
| WO | 2007116135 | A1 | 10/2007 |
| WO | 2008046109 | A2 | 4/2008 |
| WO | 2010012761 | A1 | 2/2010 |

OTHER PUBLICATIONS

Cho, Sungsik et al., Synthesis of 10-substituted triazolyl artemisinins possessing anticancer activity via Huisgen 1,3-dipolar cylcaoddition, Bioorganic & Medicinal Chemisry Letters, vol. 19, 2009, p. 382-385.
Li, Ying et al., Preparation of arteannuin derivatives containing azacyclic radical, Abstract, Shanghai Instute of Pharmaceutics, Chinese Academy of Sciences, Peop. Rep. of China, May 23, 2001, 1 pg.

*Primary Examiner* — Rebecca Anderson
*Assistant Examiner* — Karen Cheng
(74) *Attorney, Agent, or Firm* — Blank Rome LLP

(57) ABSTRACT

The present invention relates to 1,2,3-triazole containing artemisinin compounds and process for preparation thereof. Described herein is the synthesis, bioassay results and usefulness of the artemisinin derived compounds resulting from 1,3-dipolar cycloaddition reaction of artemisinin derived azide or alkyne with aliphatic or aromatic diazides. These 1,2,3-triazole containing artemisinin derived compounds embodied in this document are found to be active against various cancer cell-lines.

11 Claims, No Drawings

1,2,3-TRIAZOLE CONTAINING ARTEMISININ COMPOUNDS AND PROCESS FOR PREPARATION THEREOF

CROSS-REFERENCE TO RELATED APPLICATIONS

The present application is a national phase of International Patent Application No. PCT/IN2012/000099, filed Feb. 14, 2012, which claims priority to Indian Patent Application No. 366/DEL/2011, filed Feb. 14, 2011.

FIELD OF THE INVENTION

The invention relates to a 1,2,3-triazole containing artemisinin compounds and process for preparation thereof. The invention relates to a development of a series of novel triazole ring containing artemisinin compounds showing strong anticancer activities and processes for their preparation.

BACKGROUND OF THE INVENTION

Malaria parasite developed themselves are resistant to a variety of anti-malarial drugs which matters as a strong challenge to medicinal chemists to develop and search for new anti-malarial drugs.

The compound artemisinin, also known as Qinghaosu (QHS), isolated in 1971 from the Chinese medicinal plant *Artemisia annua* is inexpensive and used as traditional Chinese medicine against malaria.

Monomeric 1,2,4-trioxanes such as natural artemisinin have not only excellent antimalarial activities but also shows significant anticancer activities.

Artemisinin and its simple derivatives artemether, arteether and sodium artesunate have gained importance over the years as a new generation of antimalarial drugs, especially in the treatment of multi-drug resistant malaria strains.

Sodium artesunate a semisynthetic derivative of artemisinin has good tolerability, and lacks significant adverse side effects. In addition to its antimalarial activity, artesunate is cytotoxic to several cancer cell lines. They are strongly inhibitory towards a number of human cancer cell lines.

Recently artesunate was reported to inhibit CMV replication in-vitro and in a rat CMV model, exhibiting similar antiviral activity (same micromolar range) to ganciclovir, while demonstrating no cytotoxicity.

The in-vitro inhibition of clinical isolates ranged from 50-80% using 11.1 µM of artesunate. The parent substance, artemisinin, had lower anti-CMV activity compared to artesunate, suggesting that different artemisinin derivatives may have variable effects on CMV replication.

Artemisinin dimers are a new class of semi-synthetic compounds obtained by joining two artemisinin molecules without affecting the 1,2,4-trioxane ring system. Artemisinin derived 1,2,4-trioxane dimers are highly stable and its efficacy is extremely high.

In addition to this antimalarial activity, it has been shown that some artemisinin derived dimers have strong anti-cancer activities. (*J. Med. Chem.* 2003, 46, 987-994; U.S. Pat. No. 6,790,863; U.S. Pat. No. 5,677,468).

Due to the ever-growing importance of artemisinin dimers as therapeutic agents, it is necessary to focus attention on the development of novel strategies for the synthesis of artemisinin dimers.

Over the past twenty years only a few drugs isolated from higher plants have yielded clinical agents, the outstanding examples being vinblastine and vincristine from the *Madagascan periwinkle, Catharanthus roseus*, etoposide, the semi-synthetic lignam, from May-apple *Podophyllum peltatum* and the diterpenoid taxol, commonly referred to as paclitaxel, from the Pacific yew, *Taxus brevifolia*. Of these agents, paclitaxel is the most exciting, recently receiving approval from the United States Food and Drug Administration for the treatment of refractory ovarian cancer. Since the isolation of artemisinin, there has been a concerted effort by investigators to study other therapeutic applications of artemisinin and its derivatives. Because, conversion of artemisinin to dimeric form was also shown to substantially enhance anticancer activity. This class of compounds is gaining importance in the recent years because of their profound antimalarial and anticancer activity even at very low concentration. Due to the ever-growing importance of artemisinin dimers as therapeutic agents we are focusing our attention on the development of novel strategies for the synthesis of artemisinin dimers.

National Institutes of Health reported that artemisinin is inactive against P388 leukemia (See NCI Report on NSC 369397 tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian renal, prostate and breast cancers, further confirm that artemisinin displays very little anticancer activity. A series of artemisinin-related endoperoxides were tested for cytoxicity to Ehrlich ascites tumor (EAT) cells using the microculture tetrazolum (MTT) assay (H. J. Woerdenbag, et al. "Cytotoxicity of Artemisinin-Related Endoperoxides to Ehrlich Ascites Tumor Cells," *Journal of Natural Products* 1993, 56 (6), 849-856). The MTT assay, used to test the artemisinin-related endoperoxides for cytoxicity, is based on the metabolic reduction of soluble tetrazolium salts into insoluble colored formazan products by mitochondrial dehydrogenase activity of the tumor cells. As parameters for cytoxicity, the $IC_{50}$ and $IC_{80}$ values, the drug concentrations causing respectively 50% and 80% growth inhibition of the tumor cells, were used. Artemisinin, had an $IC_{50}$ value of 29.8 µM. Derivatives of dihydroartemisinin (DHA) being developed as antimalarial drugs (artemether, arteether, sodium artesunate, artelinic acid and sodium artelinate), exhibited a somewhat more potent cytoxicity. Their $IC_{50}$ values ranged from 12.2 µM to 19.9 µM. The DHA condensation by-product, disclosed previously by M. Cao, et al., 1984, was the most potent cytotoxic agent, its $IC_{50}$ being 1.4 µM. At this drug concentration the condensation by-product, is approximately twenty-two times more cytoxic than artemisinin and sixty times more cytotoxic than DHA. There is still a need, therefore, for developing structural analogs of artemisinin as antitumor agents that have potency equivalent or greater than known anticancer agents.

OBJECTS OF THE INVENTION

The main object of the present invention is to provide 1,2,3-triazole containing artemisinin compounds.

Another object of the present invention is to provide a process for preparation of 1,2,3-triazole containing artemisinin compounds.

One more object of the invention is to provide the compounds having strong anticancer activity.

Still one more object of the invention is to provide the simple process for preparation of the compounds of general formula A.

SUMMARY OF THE PRESENT INVENTION

Accordingly, the present invention provides a compound of general formula 'A' comprising

3

General formula 'A' wherein
X= wherein n=0 to 2;
Y=—(CH₂)ₙ—; n=3 to 9;
Or Y=
= or X= wherein n=1 to 2; Y=—(CH₂)ₙ—N₃; n=3 to 7;
Z=

4

In an embodiment of the invention wherein the representative compounds of general formula A comprising:

Compound 9a

Compound 9b

Compound 9c

Compound 10a
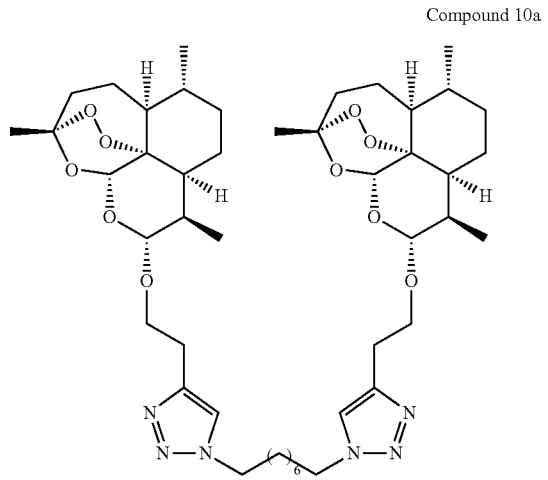
Compound 10b
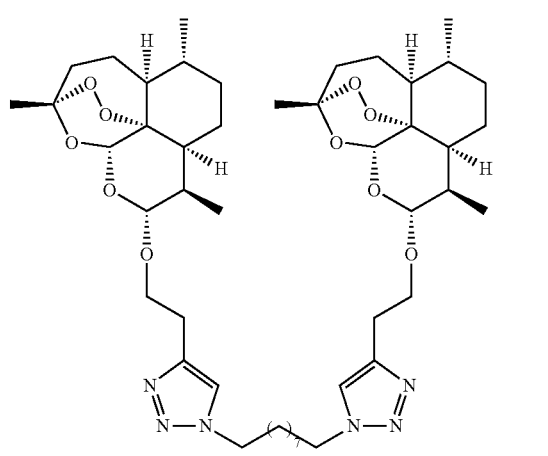
Compound 11
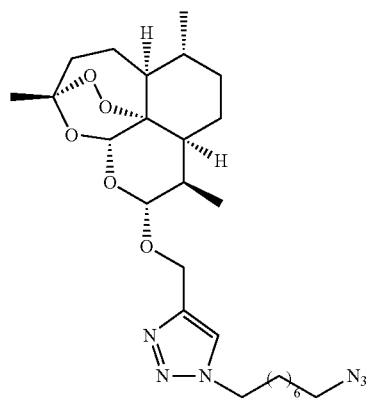
Compound 12
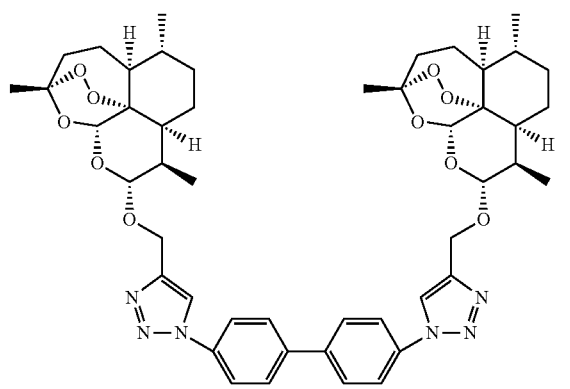
Compound 14
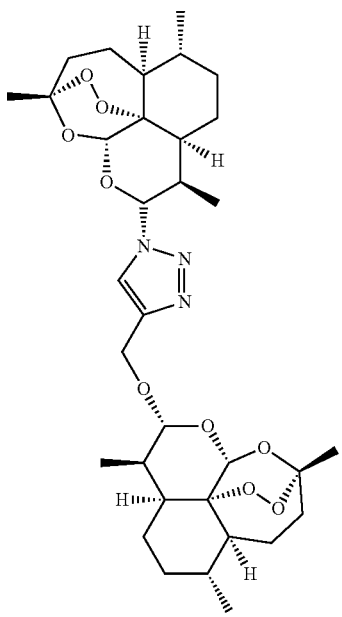
Compound 13
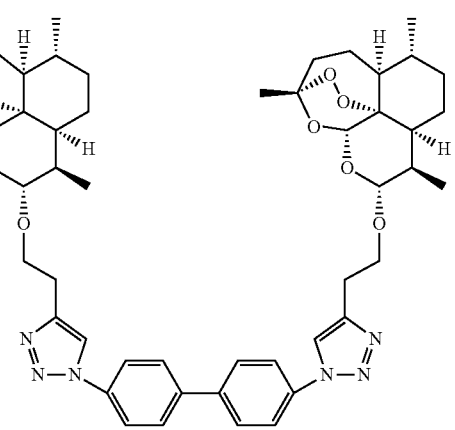

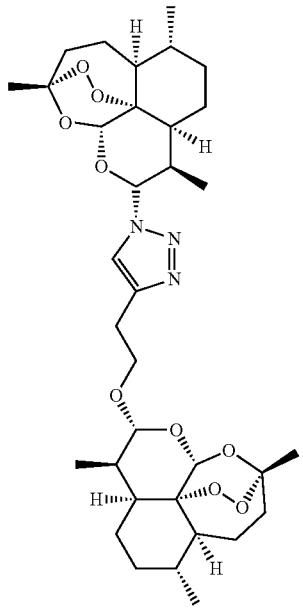

Compound 15

In another embodiment of the invention wherein the compound are useful as anticancer agents.

In still another embodiment of the invention wherein the compounds shows growth inhibition of colon HCT-15, Lung A549, Leukaemia, THP-1 and liver HEP-2 up to 97% at a concentration ranging $1 \times 10^{-5}$ to $5 \times 10^{-5}$ M.

In yet another embodiment of the invention, the compounds showed better growth inhibition of colon HCT-15, Lung A549, Leukaemia, THP-1 and liver HEP-2 cells as compared to artemisinin.

In one more embodiment of the invention wherein the process steps comprising:
(i) reacting dihydroartemisinin of formula 5 with acetylenic alcohol selected from 2-propyn-1-ol and 3-butyn-1-ol, in an organic solvent in the presence of amberlyst-15 (crosslinked styrene divinylbenzene copolymers) at a temperature in the range of 25-35° C. for a period ranging between 12-18 hrs to obtain compounds 7, 8.

5

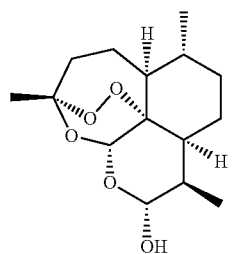

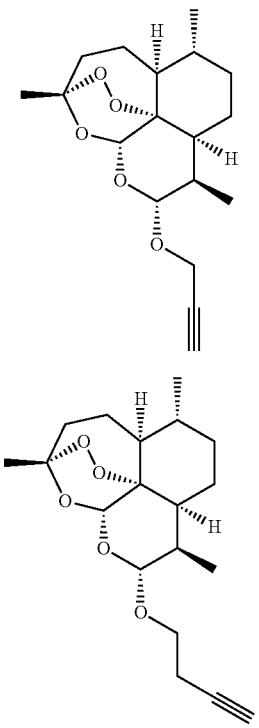

7

8

(ii) purifying the compound 7 and 8 by chromatographic methods using 5% ethylacetate in hexane as solvent,
(iii) reacting compound 7 or 8 with an azido compounds selected from a group consisting of compound no. 2a-c, 4, 6.

2a

2b

2c

4
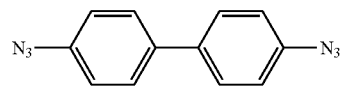

6
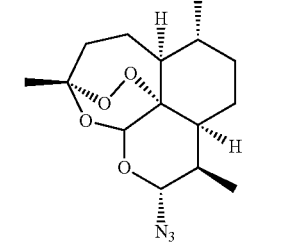

in presence of copper sulphate and sodium ascorbate in a solvent selected from a group consisting of dichloromethane and water (1:1), acetonitrile and water (1:1), chloroform and water (1:1), dimethylformamide and water (1:1) at a temperature ranging between 25-32° C., for a period ranging between 12 to 24 hour to obtain compounds of general formula A, (iv) purifying the compound of formula A using chromatographic methods.

In an embodiment of the present invention, wherein the solvent in step (i) is selected from a group consisting of dichloromethane, chloroform, 1,2-dichloroethane, nitromethane, acetonitrile.

In still another embodiment of the invention wherein the chromatographic methods used for purification of compounds of formula A are selected from a group consisting of preparative thin layer chromatography, column chromatography, HPLC, automated flash chromatography.

In still one more embodiment of the invention wherein the solvents used for the chromatographic methods selected for a group consisting of n-hexane, petroleum ether, iso-propanol, ethyl acetate, chloroform.

DETAILED DESCRIPTION OF THE PRESENT INVENTION

The problem which the present invention proposes to solve is to obtain novel artemisinin derived dimers having anticancer activities.

Most of the heterocycles correspond to interesting core structures for the synthesis of biologically active compounds.

1,2,3-Triazoles are important target molecules owing to their widespread use and importance as potent pharmacophores. Compounds containing 1,2,3-triazole moiety is more active and plays a prominent role in biological activity. In addition it is a highly efficient route in bond formations among diverse building blocks for chemical synthesis.

Our synthetic approach utilizes Huisgen 1,3-dipolar cycloaddition reaction in order to synthesize some artemisinin compounds.

We utilized some synthetic aliphatic and aromatic diazides, azo derivative of artemisinin and alkyne derivatives of artemisinin to carry out the click reactions.

A series of 1,2,3-triazole containing artemisinin derived dimers was synthesized by copper-catalyzed azide-alkyne cycloaddition (CuAAC) and afforded inhibitors of cancer cell enlargement (*Eur. J. Org. Chem.* 2006, 51-68).

Aliphatic and aromatic diazides are derived using some known reaction methods using commercially existing dihalides (*Synlett* 2005, 14, 2209). (General procedure for the synthesis of aliphatic diazides: In a round bottom flask, sodium azide (6.98 mmol) was taken in dimethyl formamide (5 mL), kept it stirring for 10 min. Dibromoalkane (3.49 mmol) was added to the system and allowed to stir for five hours. After completion of the reaction (as monitored by TLC) water was added to that mixture. Reaction mixture was washed with ether and the water was washed with ethyl acetate. Both the organic part are mixed and dried over anhydrous $Na_2SO_4$ and evaporated under reduced pressure (180 mbar). The crude product was purified by column chromatography (in hexane) to afford 2a (83%), 2b (86%) and 2c (86%) as a colourless liquids.)

The known azo derivative of artemisinin 6 has been obtained from the dihydroartemisinin in one step using sodium azide, bromo-trimethyl silane in dichloromethane under inert atmosphere (*Bioorg. Med. Chem. Lett.* 2009, 19, 382-385.).

Artemisinin derived alkynes 7, 8 have been synthesized from the known dihydroartemisinin 5 by means of some known reaction methods (*Tetrahedron Lett.* 2002, 43, 7235-7237).

Reactions of the artemisinin derived alkynes 7, 8 with different synthetic diazides 2a-c, 4 in addition to artemisinin derived azide 6 have been performed under the same reaction condition.

General Procedure for Synthesis of 9a, 9b, 9c, 10a, 10b, 11, 12 and 13

Synthetic aliphatic and aromatic diazide (0.476 mmol) and artemisinin derived alkyne (0.523 mmol) was taken in dichloromethane and water (1:1) system in a round bottom flask and stirred for few minutes. Copper sulphate (1.15 mmol) and sodium ascorbate (1.46 mmol) was added and the reaction mixture was stirred at 25° C. for 12 h. The progress of the reaction was monitored by TLC. When the reaction was completed, the crude reaction mixture was taken up in a mixture of water and dichloromethane. The aqueous layer was extracted with ethylacetate for three times. The combined organic phases were dried over anhydrous $Na_2SO_4$ and concentrated under 180 mbar. The crude product was purified by TLC (in ethylacetate).

General Procedure for Synthesis of 14 and 15

Artemisinin derived alkyne (0.645 mmol) and azido derivative of artemisinin (0.645 mmol) was taken in dichloromethane and water (1:1) system in a round bottom flask and allowed to stir. Copper sulphate (0.709 mmol) and sodium ascorbate (1.80 mmol) was added to the reaction mixture and stirring was continued at 25° C. The progress of the reaction was monitored by TLC. When the reaction was completed, water was added and the crude reaction mixture was washed with dichloromethane. The aqueous layer was extracted with ethylacetate for three times. The combined organic phases were dried over anhydrous $Na_2SO_4$ and concentrated under 180 mbar. The crude product was purified by TLC (in ethylacetate)

The present invention follows on from the highlighting by the inventors, that it is possible to prepare new artemisinin derived dimer performing Huisgen 1,3-dipolar cycloaddition reaction using synthetic diazides and azo derivative of artemisinin with artemisinin derived alkynes.

The subject of the present invention is products corresponding to the general formula 'A'.

In which

The functional moiety X represents diverse aliphatic and aromatic fragments containing 1,2,3-triazole ring system Y represents different aliphatic and aromatic linkers.

'X' joined two artemisinin moieties via different linkers (Y) without affecting the 1,2,4-trioxane ring system containing 1,2,3-triazole ring system.

The absolute stereochemistry of the C-10 centers of both the artemisinin molecules of each dimers are same as in dihydroartemisinin (*Bioorg. Med. Chem. Lett.* 2009, 19, 382-385).

The present invention also provides that the compound of the general formula 'A' is active against diverse cancer cell-lines.

The invention also provide the compound of the general formula 'A', where Y=biphenyl is showing strong activities against all cancer cell examined here than other compounds.

The compound of the formula where Y represents biphenyl is preferably given more importance due to its highest anticancer activities.

In this development, it was proved that the 1,2,4-trioxane ring system is stable under this 1,3-dipolar cycloaddition conditions. Hence this reaction can also be performed with other azides and alkynes that can be synthesized through different routes from the artemisinin molecule at different carbon positions.

In accordance with the present invention, the starting diazides were prepared according to conventional method of organic chemistry. This is illustrated in Scheme 1, in which the starting materials and reagents, when their mode of preparation is not described, are commercially available or is described in the literature or may be prepared according to methods which are described therein or which are known to persons skilled in art.

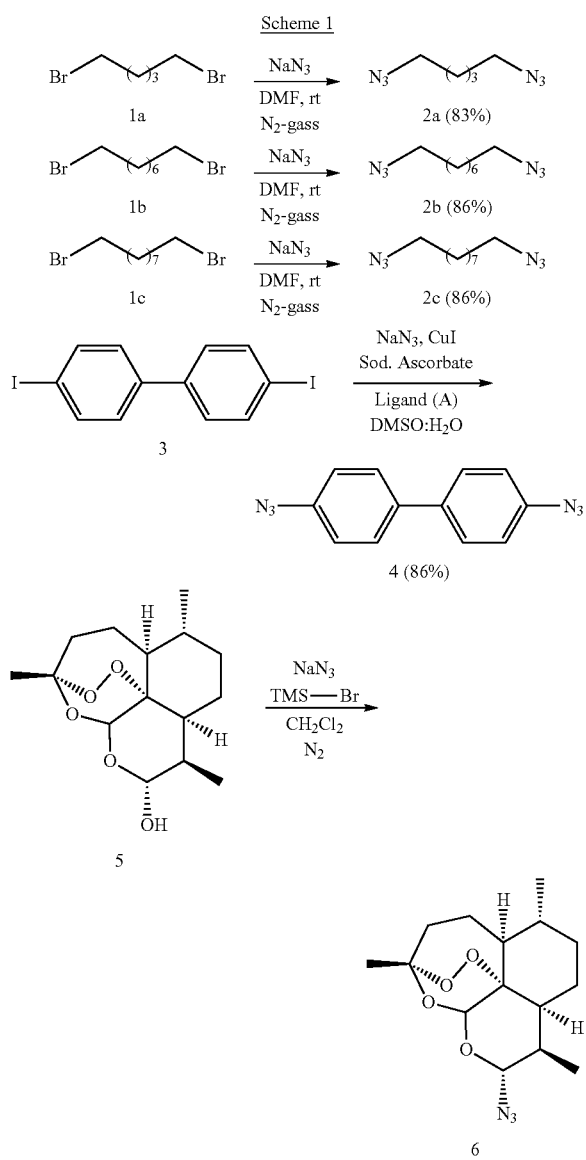

Azo derivative of artemisinin was synthesized according to the usual method of organic chemistry (*Bioorg. Med. Chem. Lett.* 2009, 19, 382-385) (Scheme 1).

Two Alkyne derivatives of artemisinin were synthesized according to the general method of organic chemistry (Scheme 1).

The invention also relates to a process for the preparation of compounds of formula 'A' defined above, characterized in that it comprises a treatment of artemisinin derived azide or alkyne with aliphatic or aromatic diazides under the same reaction conditions (Scheme 3).

The invention will be further illustrated using the detailed description of new artemisinin derived dimers, and their properties.

In Vitro Cytotoxicity Against Human Cancer Cell Lines:

The human cancer cell lines procured from National Cancer Institute, Frederick, U.S.A., were used in present study. Cells were grown in tissue culture flasks in complete growth medium (RPMI-1640 medium with 2 mM glutamine, 100 µg/mL streptomycin, pH 7.4, sterilized by filtration and supplemented with 10% fetal bovine serum and 100 units/ml penicillin before use) at 37 QC in an atmosphere of 5% $CO_2$ and 90% relative humidity in a carbon dioxide incubator. The cells at subconfluent stage were harvested from the flask by treatment with trypsin (0.05% in PBS containing 0.02% EDTA) for determination of cytotoxicity. The cell suspension of the required cell density was prepared in complete growth medium with gentamycin (50 µg/mL) for determination of cytotoxicity.

Stock solutions of $2 \times 10^{-2}$ M of test materials were prepared in DMSO. The stock solutions were serially diluted with complete growth medium containing 50 µg/ml of gentamycin to obtain working test solution of $2 \times 10^{-5}$ M to obtain final concentration of $1 \times 10^{-5}$ M respectively.

In vitro cytotoxicity against human cancer cell lines was determined (Monks et al., *J. Natl. Cancer Inst.* 1991, 83, 757-766). The 100 µL of cell suspension was added to each well of the 96-well tissue culture plate. The cells were incubated for 24 hours (at 37° C. in an atmosphere of 5% $CO_2$ and 90% relative humidity in a carbon dioxide incubator). Test materials in complete growth medium (100 µL) were added after 24 hours incubation to the wells containing cells. The plates were further incubated for 48 hours in a carbon dioxide incubator after addition of test material. The cell growth was stopped by gently layering trichloroacetic acid (50 µL, 50% w/v) on top of the medium in all the wells. The plates were incubated at 4° C. for one hour to fix the cells attached to the bottom of the wells. The liquid of all the wells was then gently decanted and discarded. The plates were washed five times with distilled water and air-dried. Cell growth was measured by staining with sulforhodamine B dye (Skehan et al., *J. Natl. Cancer Inst.* 1990, 82, 1107-1112). The adsorbed dye was dissolved in Tris-Buffer (100 µL, 0.01M, pH 10.4) and plates were gently stirred for 10 minutes on a mechanical stirrer. The optical density (OD) was recorded on ELISA reader at 540 nm.

The cell growth was calculated by subtracting mean OD value of respective blank from the mean OD value of experimental set. Percent growth in presence of test material was calculated considering the growth in absence of any test material as 100% and in turn percent growth inhibition in presence of test material was calculated. Suitable blank, controls and positive controls were included in the study.

All compounds reported here have been tested for in vitro anticancer activity against three cancer cell lines and some of them have shown encouraging results. Compound 12, 13, and 15 show 75%, 56% and 66% growth inhibition at $1 \times 10^{-5}$ M against colon HCT-15 human cancer cell line. The compound 10b, 11, 12 and 15 are also promising to give up to 60%, 64%, 64% and 48% GI at $5 \times 10^{-5}$ M against Lung cancer cell A-549. Among other compounds, the compound 10b shows glimpses of superior activity (GI 71% at $5 \times 10^{-5}$ M) against human liver cell line of HEP-2 type which is comparable with the mitomycin-c (GI 58% at $1 \times 10^{-5}$ M concentration). On the other hand the compound 10b, 11, 12, 13 and 15 show excellent 97%, 95%, 80%, 82% and 79% growth inhibition at $5 \times 10^{-5}$ M against leukaemia THP-1 which are comparable with 5-Fluorouracil (GI 73% at $2 \times 10^{-5}$ M concentration). Overall, the compound 12 is showing promising activity results against almost all three cancer cell lines (colon HCT-15, Lung A-549 and leukaemia THP-1) tested herein. The in vitro anticancer activity results are summarized in Table 1.

TABLE 1

In vitro anticancer activity.

| Compound | Conc (M) | colon HCT-15 | Lung A-549 | leukaemia THP-1 | Liver HEP-2 |
|---|---|---|---|---|---|
| | | % GROWTH INHIBITION | | | |
| 10a | $5 \times 10^{-5}$ | 25 | 32 | 68 | 39 |
| 10b | $5 \times 10^{-5}$ | 51 | 60 | 97 | 71 |
| 11 | $5 \times 10^{-5}$ | 49 | 64 | 95 | 54 |
| 12 | $5 \times 10^{-5}$ | 78 | 64 | 80 | — |
| 13 | $5 \times 10^{-5}$ | 66 | 46 | 82 | — |
| 14 | $5 \times 10^{-5}$ | 63 | 22 | 62 | — |
| 15 | $5 \times 10^{-5}$ | 70 | 48 | 79 | — |
| Artemisinin | $5 \times 10^{-5}$ | 31 | 29 | — | — |
| Artemisinin | $1 \times 10^{-5}$ | 29 | 19 | — | — |
| 5-Fluorouracil | $2 \times 10^{-5}$ | 65 | — | 73 | — |
| Mitomycin-c | $1 \times 10^{-5}$ | — | — | — | 58 |
| 12 | $1 \times 10^{-5}$ | 75 | 56 | 75 | — |
| 13 | $1 \times 10^{-5}$ | 56 | 41 | 63 | — |
| 15 | $1 \times 10^{-5}$ | 66 | 29 | 78 | — |

$^1$H NMR and $^{13}$C NMR spectra were recorded using a Bruker DPX-300 NMR machine. IR spectra were recorded on a Perkin-Elmer 1640 FT-IR spectrometer. Optical rotations were measured on a Perkin-Elmer 343 polarimeter. Mass spectra were recorded on WATERS Micro-mass ZQ 4000 (ESI Probe) spectrometer. Melting points are uncorrected and recorded on Buchi B-540 melting point apparatus. Column chromatography was performed with Merck silica gel (100-200 mesh) and preparative TLC was carried out on plates prepared with Merck Silica gel G. Moisture sensitive reactions were conducted under a dry nitrogen atmosphere. All solvents were distilled at their boiling point, and other commercially available reagents were used as received, unless otherwise stated.

Following examples are given by way of illustration and should not be construed to limit the scope of the invention.

Example

Synthesis of the Diazo Aliphatic Linkers 2a-c:

Treatment of the dibomoaliphatic compound 1a-c (e.g. 1,5-dibromopentane, 1,8-dibromooctane and 1,9-dibromononane) with sodium azide in dimethyl formamide under nitrogen atmosphere furnished the desired diazoliphatics 2a-c (e.g. 1,5-diazopentane, 1,8-diazooctane and 1,9-diazononane).

General Procedure: In a round bottom flask taken sodium azide (6.98 mmol) in dimethyl formamide (5 ml) and keep it stirring for 10 min. After that added dibromoalkane (3.49 mmol) to that system and allowed to stir for five hours at 25° C. After completion of the reaction (monitoring by TLC) water was added to that mixture. Reaction mixture was washed with ether and the water was washed with ethyl acetate. Both the organic part are mixed and dried over anhydrous NaSO4 and evaporated under 180 mbar. The crude product was purified by column chromatography (in hexane) to get the pure compounds i.e., 2a (83%), 2b (86%) and 2c (86%) as a colourless liquids.

The dibromoalkanes used for the synthesis of 2a, 2b and 2c are 1,5-dibromopentane, 1,8-dibromooctane and 1,9-dibromononane respectively.

Synthesis of the Diazo Aromatic Linker 4:

4,4'diiodobiphenyl 3 on handling with sodium azide, cuprous iodide, sodium ascorbate, N,N'-Dimethyl-ethane-1, 2-diamine (B) in dimethyl sulfoxide and water system furnished the required 4,4' diazobiphenyl 4.

Procedure: 4,4'diiodobiphenyl (0.492 mmol), sodium azide (1.03 mmol), sodium ascorbate (0.0246 mmol), cuprous iodide (0.0492 mmol), ligand, (N,N'-Dimethyl-ethane-1,2-diamine) (0.0738 mmol) and 0.984 ml DMSO-H$_2$O (5:1) were introduced into a two necked round bottom flask equipped with a stirring bar. After it was degassed, and then introduced under an argon atmosphere, the reaction mixture was stirred at 25° C., and the advancement of the reaction was followed by TLC. When the reaction was completed, the crude reaction mixture was taken up in a mixture of brine and ethylacetate. The aqueous phase was extracted with ethylacetate for three times. The combined organic phases were dried out over anhydrous Na$_2$SO$_4$ and concentrated under 180 mbar. The crude product was purified by column chromatography (1% EtOAc in hexane) to afford 4 (86%) as yellow solid.

Synthesis of the Azo Derivative of Artemisinin 6:

It can be prepared by known method using dihydroartemisinin in presence of trimethylsilyl bromide (2.2 equiv) and sodium azide (3 equiv) at room temperature (*Bioorg. Med. Chem. Lett.* 2009, 19, 382-385).

Synthesis of the Alkyne Derivatives of Artemisinin 7 and 8:

Two alkyne derivatives of artemisinin 7 and 8 were synthesized by employing Amberlyst-15 in dry dichloromethane at room temperature under inert atmosphere to afford 7 and 8.

Procedure:

Compound 5 (3.54 mmol) and acetylenic alcohol (2-propyn-1-ol and 3-butyn-1-ol) (3.54 mmol) were dissolved in 10 ml dry dichloromethane and 800 mg Amberlyst-15 was added to the same under the nitrogen atmosphere and stirred for overnight at 25° C. The reaction was monitored by TLC. After completion of the reaction, the dichloromethane was filtered, dried in excess of anhydrous Na$_2$SO$_4$, concentrated the filtrate under 180 mbar and the crude combination was purified by column chromatography (5% EtOAc in Hexane) to afford 7 (67%) and 8 (65%) as white solid.

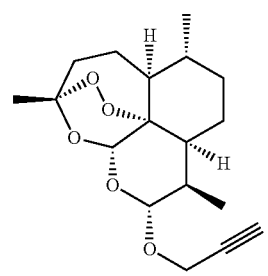

7

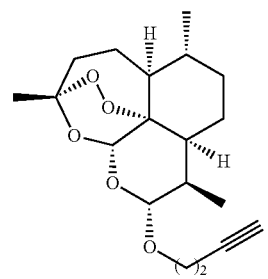

8

Acetylenic alcohol used for the preparation of 7 and 8 are 2-propyn-1-ol and 3-butyn-1-ol respectively.

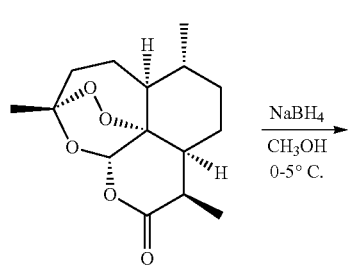

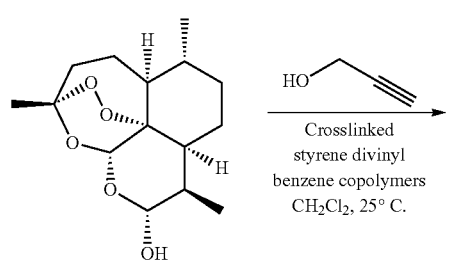

7 (67%)

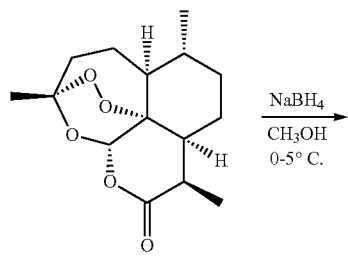

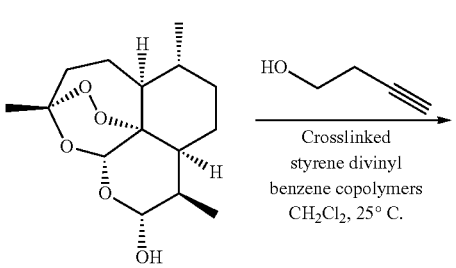

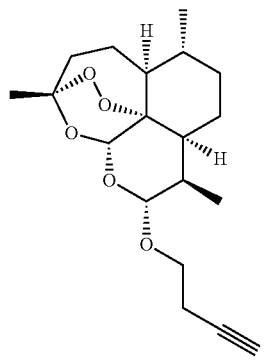

8 (65%)

Synthesis of the Artemisinin Derived Dimers 9a, 9b, 9c, 10a, 10b, 12 and 13 in Addition of a Monomer 11:

On treatment of synthetic diazides with artemisinin derived alkynes in the presence of copper sulphate and sodium ascorbate in dichloromethane and water system at room temperature.

Procedure:

Synthetic diazide (0.476 mmol) and artemisinin derived alkyne 7 or 8 (0.523 mmol) were taken in an equal mixture of dichloromethane (10 mL) and water (10 mL) in a round bottom flask. Copper sulphate (1.15 mmol) and sodium ascorbate (1.46 mmol) was added to the same. The reaction mixture was stirred at 25° C. The progress of the reaction was monitored by TLC. When the reaction was completed, the crude reaction mixture was taken in a separating funnel and the dichloromethane layer was separated out. The aqueous layer was extracted with ethyl acetate (3×20 mL). The combined organic phases were dried over anhydrous $Na_2SO_4$ and concentrated under 180 mbar. The crude product was purified by TLC (in ethylacetate) to afford 9a (36%), 9b (38%), 9c (41%), 10a (40%), 10b (39%), 11 (50%), 12 (40%), 13 (40%).

The Artemisinin derived alkyne 7 was used for preparation of compounds 9a-9c, 11, and 13 whereas the other artemisinin derived alkyne 8 was used for preparation of compounds 10a-10b and 12.

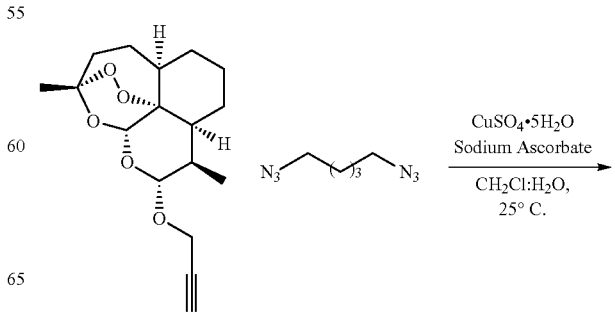

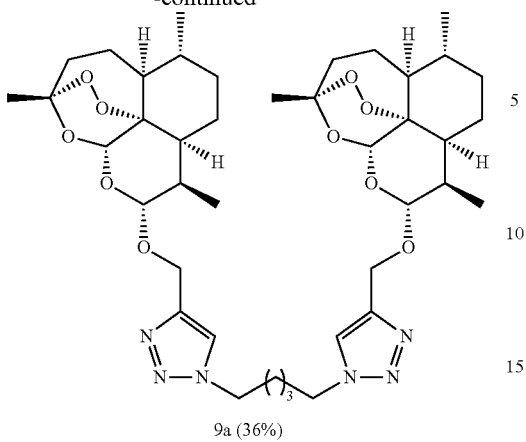
9a (36%)
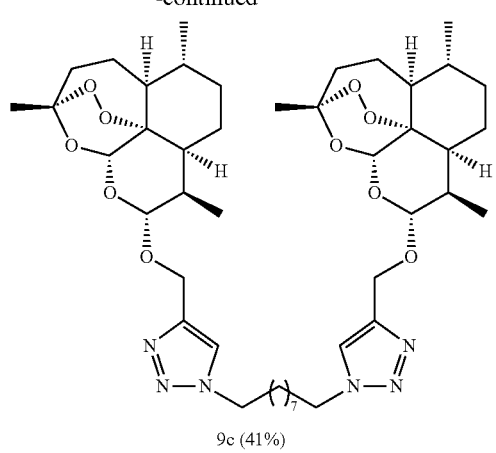
9c (41%)
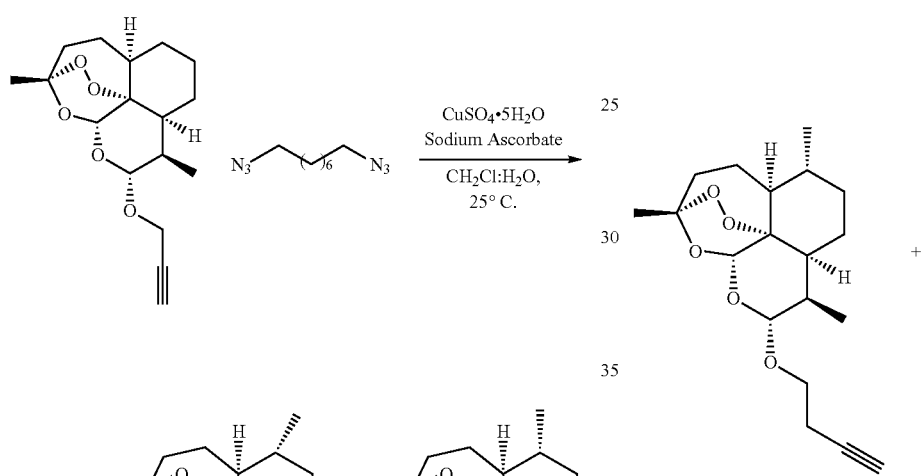
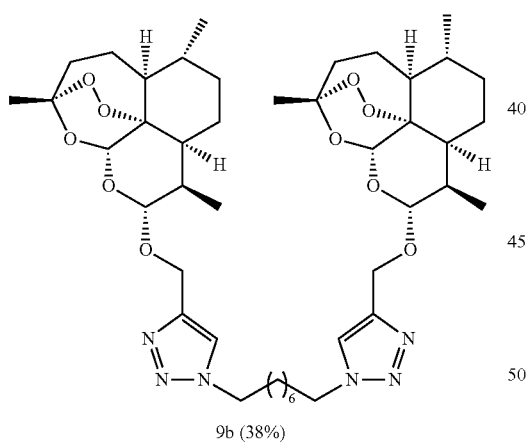
9b (38%)
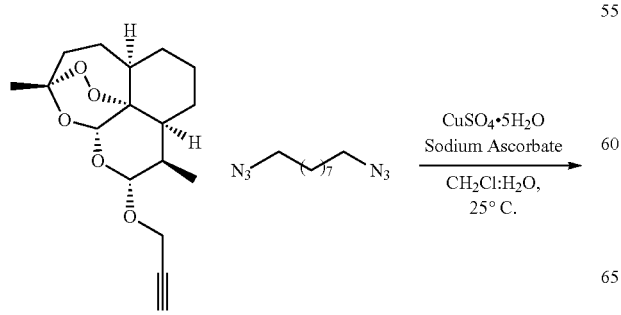
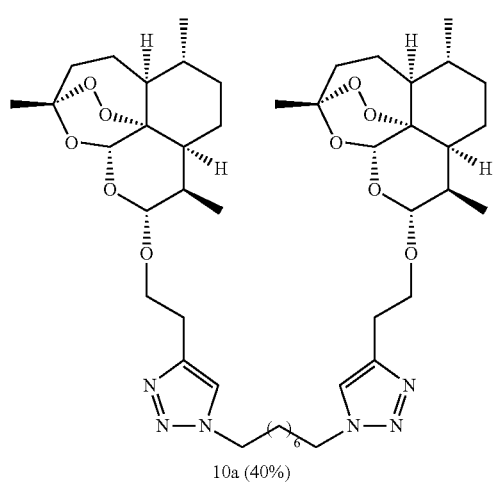
10a (40%)

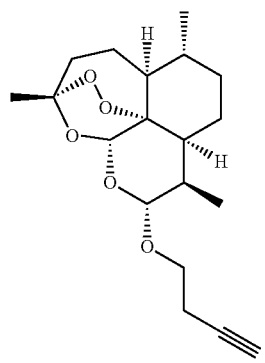
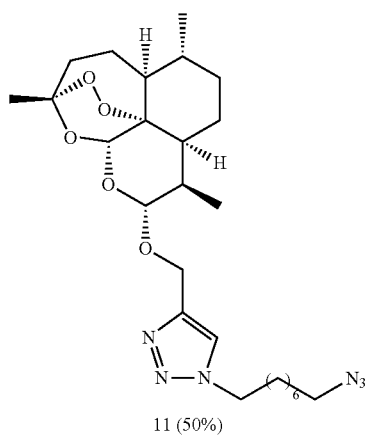
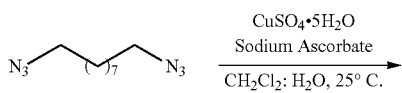
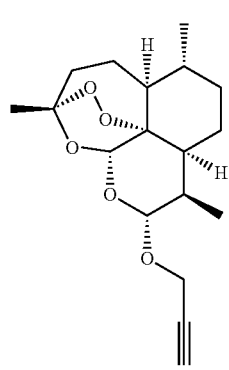
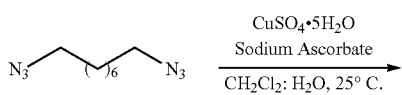

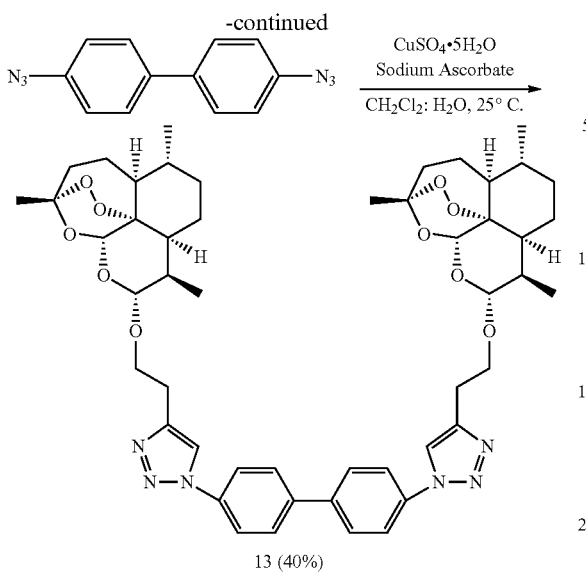

13 (40%)

Compound 9a (Artemisinin Dimer)
Colourless Gummy
$[\alpha]_D^{20}$ (c 2.05, CHCl$_3$)=+45.14
$^1$H NMR (300 MHz, CDCl$_3$) δ 7.54 (s, 1H, triazol), 7.44 (s, 1H, triazol), 5.42 (s, 1H, H-12), 4.93 (d, 1H, J=15.6 Hz, H-10), 4.89 (s, 1H, H-12'), 4.68 (d, 1H, J=12.6 Hz, H-10'), 4.35 (m, 4H, —OCH$_2$—), 2.36-1.70 (m, 24H, arte aliphatic), 1.45 (s, 6H, Me-3, Me-3'), 1.25 (s, 10H, aliphatic chain), 0.95 (d, 6H, J=6 Hz, Me-9, Me-9'), 0.88 (d, 6H, J=7.3 Hz, Me-6, Me-6') ppm.
$^{13}$C NMR (75 MHz, CDCl$_3$) b 148.1, 145.0, 122.4, 121.8, 104.1, 101.4, 87.9, 81.1, 61.4, 56.2, 56.0, 52.4, 49.7, 49.6, 44.3, 41.0, 37.3, 36.3, 34.5, 30.7, 30.3, 29.6, 29.3, 29.2, 28.7, 26.1, 24.6, 24.4, 22.9, 20.5, 20.3, 12.9 ppm.
IR (CHCl$_3$) ν 2924, 1453, 1219, 772 cm$^{-1}$
ESIMS: 762.2 (M$^+$-60+Na)
Analysis calculated for C$_{41}$H$_{62}$N$_6$O$_{10}$ C, 61.63; H, 7.82; N, 10.52. Found C, 61.61; H, 7.72; N, 10.42.
Compound 9b (Artemisinin Dimer)
Colourless Gummy
$[\alpha]_D^{20}$ (c 0.55, CHCl$_3$)=+16.61
$^1$H NMR (300 MHz, CDCl$_3$) δ 7.53 (s, 1H, triazol), 7.48 (s, 1H, triazol), 5.42 (s, 1H, H-12), 4.94 (d, 1H, J=15.1 Hz, H-10), 4.9 (s, 1H, H-12'), 4.7 (d, 1H, J=12.5 Hz, H-10'), 4.37 (t, 4H, J=6.9 Hz, —OCH$_2$—), 2.6 (m, 4H, aliphatic chain), 2.6-1.49 (m, 24H, arte aliphatic), 1.4 (s, 6H, Me-3, Me-3'), 1.30 (s, 12H, aliphatic), 0.94 (d, 6H, J=6 Hz, Me-9, Me-9'), 0.88 (d, 6H, J=7.3 Hz, Me-6, Me-6') ppm.
$^{13}$C NMR (75 MHz, CDCl$_3$) δ 169.4, 145.4, 121.4, 121.3, 107.9, 102.0, 100.0, 93.6, 88.2, 84.0, 80.4, 68.6, 67.4, 67.1, 61.5, 55.5, 50.2, 50.1, 50.0, 46.7, 42.3, 35.7, 34.7, 33.2, 30.6, 30.2, 30.1, 29.0, 28.7, 28.6, 27.6, 26.5, 26.4, 26.3, 24.6, 21.6, 21.0, 20.5, 18.8, 12.4 ppm. IR (CHCl$_3$) ν 2923, 2850, 1216, 771 cm$^{-1}$
ESIMS: 841 (M$^+$)
Analysis calculated for C$_{44}$H$_{68}$N$_6$O$_{10}$ C, 62.82; H, 8.15; N, 9.99. Found C, 62.45; H, 8.21; N, 9.89.
Compound 9c (Artemisinin Dimer)
Colourless Gummy
$[\alpha]_D^{20}$ (c 1.5, CHCl$_3$)=+9.2
$^1$H NMR (300 MHz, CDCl$_3$) δ 7.57 (s, 1H, triazol), 7.50 (s, 1H, triazol), 5.26 (s, 1H, H-12), 4.94 (d, 1H, J=8.5 Hz, H-10), 4.88 (s, 1H, H-12'), 4.66 (d, 1H, J=12.6 Hz, H-10'), 4.34 (t, 4H, J=7 Hz, —OCH$_2$—), 3.57 (m, 2H, H-9, H-9'), 2.45 (m, 4H, H-4, H-4'), 2.45-1.66 (m, 18H, arte aliphatic), 1.55 (s, 6H, Me-3, Me-3'), 1.28 (s, 18H, aliphatic chain), 0.92 (d, 6H, J=7.6 Hz, Me-9, Me-9'), 0.87 (d, 6H, J=6.3 Hz, Me-6, Me-6') ppm.
$^{13}$C NMR (75 MHz, CDCl$_3$) δ 147.7, 145.0, 122.2, 121.6, 108.0, 99.0, 93.7, 84.1, 77.4, 77.2, 77.0, 76.6, 69.48, 61.6, 56.3, 50.3, 50.2, 42.3, 40.5, 34.8, 34.6, 30.3, 30.18, 29.6, 29.0, 28.6, 26.2, 26.0, 24.9, 21.0, 18.8, 12.3 ppm.
IR (CHCl$_3$) ν 2922, 2851, 1456, 1219, 772 cm$^{-1}$
ESIMS: 855 (M$^+$+Na)
Analysis calculated for C$_{45}$H$_{70}$N$_6$O$_{10}$ C, 63.21; H, 8.25; N, 9.83. Found C, 63.45; H, 8.12; N, 9.91.
Compound 10a (Artemisinin Dimer)
Colourless Gummy
$[\alpha]_D^{20}$ (c 1.15, CHCl$_3$)=+15.7
$^1$H NMR (300 MHz, CDCl$_3$) δ 7.45 (s, 1H, triazol), 7.31 (s, 1H, triazol), 6.2 (s, 1H, H-12), 5.1 (s, 1H, H-12'), 4.77 (d, 1H, J=4.2 Hz, H-10), 4.75 (d, 1H, J=4.2 Hz, H-10', 4.32 (t, 4H, J=7.17 Hz, aliphatic chain), 3.9 (m, 4H, —OCH$_2$CH$_2$—), 3.59 (m, 2H, H-9, H-9'), 2.9 (m, 4H, —OCH$_2$CH$_2$—), 2.4-1.6 (m, 22H, arte aliphatic), 1.55 (s, 6H, Me-3, Me-3'), 1.3 (s, 12H, aliphatic), 0.91 (d, 6H, J=3.6 Hz, Me-9, Me-9'), 0.86 (d, 6H, J=2.8 Hz, Me-6, Me-6') ppm.
$^{13}$C NMR (75 MHz, CDCl$_3$) δ 170.0, 147, 146, 121.3, 107.9, 100.0, 93.6, 88.3, 84.0, 80.4, 69.5, 67.5, 55.5, 50.1, 46.8, 42.4, 40.5, 35.8, 34.7, 33.2, 30.6, 30.3, 29.6, 28.7, 26.3, 24.9, 24.6, 21.6, 21.0, 20.5, 18.8, 12.4 ppm.
IR (CHCl$_3$) ν 2926, 2867, 1453, 1220, 1017, 772 cm$^{-1}$
ESIMS: 809 (M$^+$–60)
Analysis calculated for C$_{46}$H$_{72}$N$_6$O$_{10}$ C, 63.57; H, 8.35; N, 9.67. Found C, 63.42; H, 8.31; N, 9.59.
Compound 10b (Artemisinin Dimer)
Colourless Gummy
$[\alpha]_D^{20}$ (c 2.0, CHCl$_3$)=+18.6
$^1$H NMR (300 MHz, CDCl$_3$) δ 7.45 (s, 1H, triazol), 7.32 (s, 1H, triazol), 6.02 (s, 1H, H-12), 5.1 (s, 1H, H-12'), 4.77 (d, 1H, J=4.3 Hz, H-10), 4.49 (d, 1H, J=4.19 Hz, H-10'), 4.29 (t, 4H, J=7 Hz, aliphatic chain), 3.56 (m, 2H, H-9, H-9'), 3.02 (m, 4H, —OCH$_2$CH$_2$—), 1.86-1.64 (m, 22H, arte. aliphatic), 1.55 (s, 6H, Me-3, Me-3'), 1.29 (s, 18H, aliphatic chain), 0.94 (d, 6H, J= . . . Hz, Me-9, Me-9'), 0.87 (d, 6H, J= . . . Hz, Me-6, Me-6') ppm.
$^{13}$C NMR (75 MHz, CDCl$_3$) δ 169.4, 145.5, 145.3, 121.2, 107.9, 102.0, 100.0, 93.6, 88.3, 84.0, 80.4, 69.4, 68.6, 67.5, 67.2, 55.5, 50.1, 50.0, 46.7, 42.4, 40.5, 35.7, 34.7, 33.2, 30.6, 30.3, 29.1, 28.9, 27.7, 26.5, 26.4, 24.9, 24.6, 21.6, 21.0, 20.5, 18.8, 12.46, 12.41 ppm.
IR (CHCl$_3$) ν 2926, 2870, 1457, 1220, 1018, 772 cm$^{-1}$
ESIMS: 883.7 (M$^+$)
Analysis calculated for C$_{47}$H$_{74}$N$_6$O$_{10}$ C, 63.92; H, 8.45; N, 9.52. Found C, 63.91; H, 8.31; N, 9.48.
Compound 11
Colourless Gummy
$[\alpha]_D^{20}$ (c 2.35, CHCl$_3$)=+72.28
$^1$H NMR (300 MHz, CDCl$_3$) δ 7.48 (s, 1H, triazol), 5.42 (s, 1H, H-12), 4.95 (d, 1H, J=9.51 Hz, H-10), 4.91 (s, 2H, —OCH$_2$—), 4.34 (t, 2H, J=7.1 Hz, —CH$_2$— triazol end), 3.28 (t, 2H, J=6.8 Hz, —CH$_2$—N$_3$ end), 2.64 (m, 1H, H-9), 2.3 (td, 2H, H-4), 2.05-1.56 (m, 9H, arte aliphatic), 1.45 (s, 3H, Me-3), 1.33 (s, 12H, aliphatic chain), 0.94 (d, 3H, J=6 Hz, Me-9), 0.89 (d, 3H, J=7.3 Hz, Me-6) ppm.
$^{13}$C NMR (75 MHz, CDCl$_3$) δ 144.9, 122.2, 104.1, 101.5, 87.9, 81.1, 77.2, 61.6, 52.5, 51.3, 50.1, 44.3, 37.3, 36.4, 34.5, 30.8, 30.2, 28.9, 28.8, 28.7, 26.5, 26.3, 26.1, 24.6, 24.4, 20.3, 12.9 ppm.

IR (CHCl$_3$) ν 2923, 2852, 2095, 1458, 1051, 1009, 875 cm$^{-1}$

ESIMS: 518 (M$^+$)

Analysis calculated for C$_{26}$H$_{42}$N$_6$O$_5$ C, 60.21; H, 8.12; N, 16.2. Found C, 60.11; H, 8.41; N, 16.01.

Compound 12

Colourless Gummy $[\alpha]_D^{20}$ (c 3.1, CHCl$_3$)=+29.5

$^1$H NMR (300 MHz, CDCl$_3$) δ 8.02 (s, 1H, triazol), 8.0 (s, 1H, triazol), 7.89 (m, 4H, phenyl), 7.80 (m, 4H, phenyl), 5.47 (s, 1H, H-12), 5.34 (s, 1H, H-12'), 5.06 (d, 1H, J=4.6 Hz, H-10), 4.97 (d, 1H, J=4.3 Hz, H-10'), 5.0 (s, 2H, —OCH$_2$), 4.77 (s, 2H, —OCH$_2$'), 3.59 (m, 2H, H-9, H-9'), 2.38 (td, 4H, H-4, H-4'), 2.17-1.74 (m, 18H, atre aliphatic), 1.25 (s, 6H, Me-3, Me-3'), 0.93 (d, 6H, J=2.7 Hz, Me-9, Me-9'), 0.89 (d, 6H, J=3.1 Hz, Me-6, Me-6') ppm.

$^{13}$C NMR (75 MHz, CDCl$_3$) δ 145.99, 145.9, 140.0, 136.6, 128.3, 120.97, 120.7, 120.5, 108.0, 104.2, 101.8, 99.4, 93.8, 88.0, 84.1, 81.1, 77.2, 69.5, 61.5, 52.4, 44.3, 42.4, 40.6, 37.3, 36.3, 34.8, 34.6, 34.5, 30.8, 30.3, 29.7, 26.1, 25.0, 24.6, 24.4, 21.0, 20.3, 18.8, 13.0, 12.3 ppm.

IR (CHCl$_3$) ν 2921, 1449, 1219, 1020, 772 cm$^{-1}$

ESIMS: 881 (M$^+$)

Analysis calculated for C$_{48}$H$_{60}$N$_6$O$_{10}$ C, 65.44; H, 6.86; N, 9.54. Found C, 65.35; H, 6.81; N, 9.42.

Compound 13

Colourless Gummy $[\alpha]_D^{20}$ (c 2.3, CHCl$_3$)=+33.3

$^1$H NMR (300 MHz, CDCl$_3$) δ 7.88 (s, 1H, triazol), 7.86 (s, 1H, triazol), 7.85 (m, 4H, phenyl), 7.78 (m, 4H, phenyl), 5.26 (s, 1H, H-12), 5.18 (s, 1H, H-12'), 4.86 (d, 1H, J=3.3 Hz, H-10), 4.82 (d, 1H, J=4.1 Hz, H-10'), 3.75 (m, 4H, —OCH$_2$CH$_2$—), 3.57 (m, 2H, H-9, H-9'), 3.13 (m, 4H, —OCH$_2$CH$_2$), 2.21-1.63 (m, 22H, arte aliphatic), 1.43 (s, 6H, Me-3, Me-3'), 0.90 (d, 6H, J=7.9 Hz, Me-9, Me-9'), 0.80 (d, 6H, J=6.3 Hz, Me-6, Me-6') ppm.

$^{13}$C NMR (75 MHz, CDCl$_3$) δ 146.4, 139.8, 136.7, 128.3, 128.2, 120.6, 119.5, 107.9, 104.0, 101.8, 100.1, 93.5, 87.8, 84.0, 81.0, 77.2, 69.5, 67.1, 67.0, 52.4, 44.2, 42.4, 40.5, 37.3, 36.3, 34.7, 34.5, 30.8, 30.3, 30.2, 29.6, 26.5, 26.1, 24.9, 24.6, 24.3, 21.0, 20.2, 18.8, 13.0, 12.4 ppm.

IR (CHCl$_3$) ν 2924, 1508, 1021, 825, 771 cm$^{-1}$

ESIMS: 909 (M$^+$)

Analysis calculated for C$_{50}$H$_{64}$N$_6$O$_{10}$ C, 66.06; H, 7.10; N, 9.24. Found C, 66.12; H, 7.04; N, 9.21.

Synthesis of the Artemisinin Derived Dimers 14 and 15:

On treatment of artemisinin derived azide 6 with artemisinin derived alkynes (7 & 8) in the presence of copper sulphate and sodium ascorbate in dichloromethane and water system at room temperature. These two compounds are artemisinin dimers, but the binding at one of the artemisinin moiety is at nitrogen (N) of the triazole moiety as shown in general formula 'A'.

Procedure:

Artemisinin derived alkyne 7 or 8 (0.645 mmol) and artemisinin derived azide 6 (0.645 mmol) was taken in an equal mixture of dichloromethane (10 mL) and water (10 mL) in a round bottom flask. Copper sulphate (0.709 mmol) and sodium ascorbate (1.80 mmol) was added to the same. The reaction mixture was stirred at 25° C. The progress of the reaction was monitored by TLC. When the reaction was completed, the crude reaction mixture was taken a separating funnel and the dichloromethane layer was separated out. The aqueous layer was extracted with ethyl acetate (3×20 mL). The combined organic phases were dried over anhydrous Na$_2$SO$_4$ and concentrated under 180 mbar. The crude product was purified by preparative TLC (in ethylacetate) to afford 14 (39%) or 15 (38%).

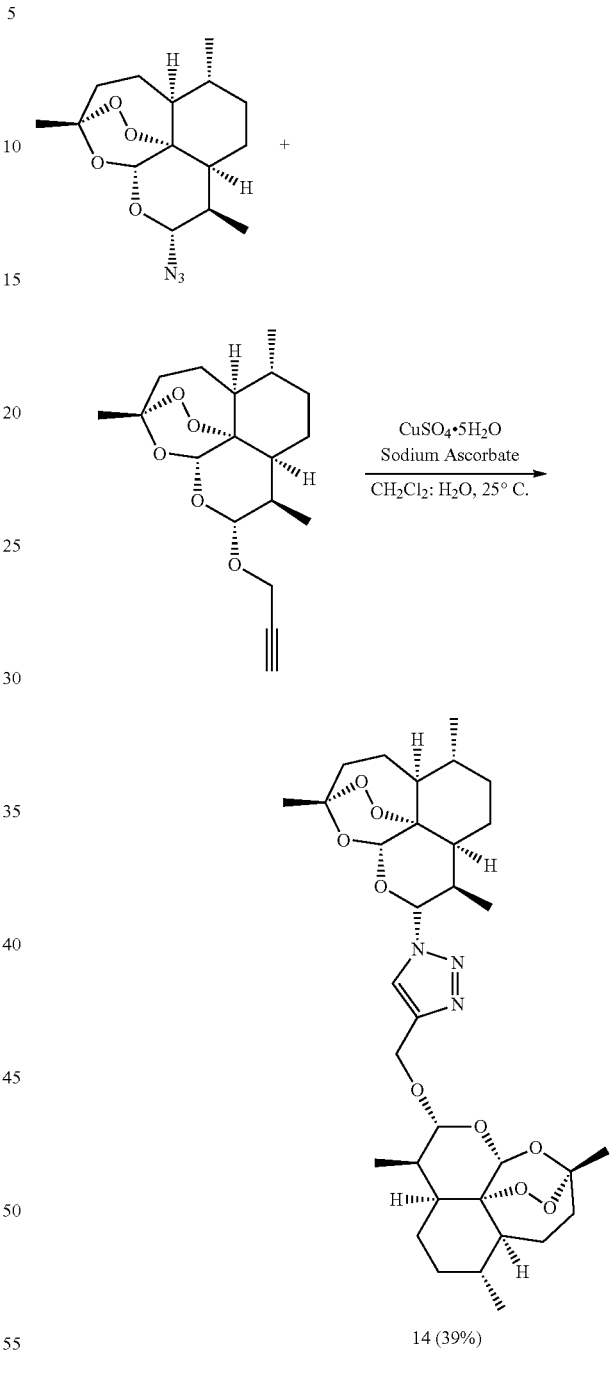

14 (39%)

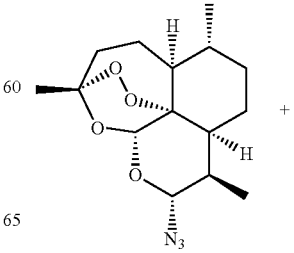

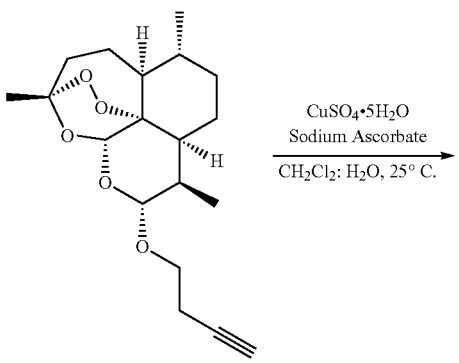

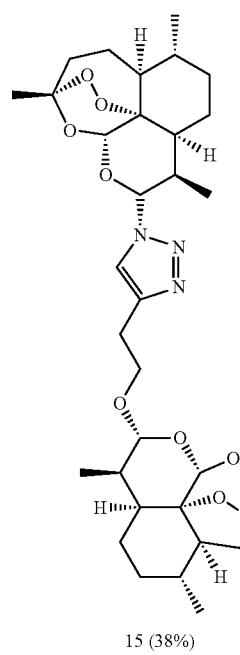

15 (38%)

Compound 14
Colourless Gummy
[α]$_D^{20}$ (c 1.8, CHCl$_3$)=−13.5

$^1$H NMR (300 MHz, CDCl$_3$) δ 7.7 (s, 1H, triazol), 5.86 (d, 1H, J=10.7 Hz, H-10), 5.45 (s, 1H, H-12), 5.27 (s, 1H, H-12'), 4.89 (d, 1H, J=4.2 Hz, H-10'), 4.86 (s, 2H, —OCH$_2$—), 3.59 (m, 2H, H-9, H-9'), 2.87-1.25 (m, 22H, arte aliphatic), 0.93 (s, 3H, Me-3), 0.908 (s, 3H, Me-3'), 0.86 (d, 6H, J=6.3 Hz, Me-9, Me-9'), 0.79 (d, 6H, J=7 Hz, Me-6, Me-6') ppm.

$^{13}$C NMR (75 MHz, CDCl$_3$) δ 145.7, 119.9, 109.0, 108:0, 104.8, 99.7, 95.9, 93.6, 86.7, 84.1, 83.4, 79.8, 76.3, 69.5, 69.1, 61.7, 51.4, 42.5, 41.6, 40.6, 37.3, 34.8, 34.7, 33.9, 32.0, 30.2, 29.6, 29.3, 25.7, 25.0, 24.5, 22.3, 21.0, 20.1, 18.8, 18.6, 12.4, 12.2 ppm.

IR (CHCl$_3$) ν 2924, 1453, 1383, 1017, 930 cm$^{-1}$
ESIMS: 631 (M$^+$)
Analysis calculated for C$_{33}$H$_{49}$N$_3$O$_9$ C, 62.74; H, 7.82; N, 6.65. Found C, 62.71; H, 7.71; N, 6.60.

Compound 15
Colourless Gummy
[α]$_D^{20}$ (c 1.7, CHCl$_3$)=−10.8

$^1$H NMR (300 MHz, CDCl$_3$) δ 7.55 (s, 1H, triazol), 5.83 (d, 1H, J=10.2 Hz, H-10), 5.44 (s, 1H, H-12), 5.22 (s, 1H, H-12'), 4.77 (d, 1H, J=4.1 Hz, H-10'), 4.1 (m, 2H, —OCH$_2$CH$_2$—), 3.56 (m, 2H, H-9, H-9'), 2.99 (m, 2H, —OCH$_2$CH$_2$—), 2.05-1.25 (m, 22H, arte aliphatic), 0.94 (s, 3H, Me-3), 0.92 (s, 3H, Me-3'), 0.87 (d, 6H, J=2.7 Hz, Me-9, Me-9'), 0.74 (d, 6H, J=7 Hz, Me-6, Me-6') ppm.

$^{13}$C NMR (75 MHz, CDCl$_3$ δ 169.4, 145.5, 121.4, 121.3, 102, 88.3, 68.6, 67.2, 61.6, 55.6, 50.1, 50, 46.8, 35.8, 33.2, 30.6, 30.2, 30.1, 29.7, 28.6, 27.7, 26.4, 26.2, 1024.6, 21.6, 20.5, 12.4 ppm.

IR (CHCl$_3$) ν 2925, 1454, 1383, 1220, 1019, 928, 772 cm$^{-1}$
ESIMS: 668 (M$^+$+Na)
Analysis calculated for C$_{34}$H$_{51}$N$_3$O$_9$ C, 63.24; H, 7.96; N, 6.51. Found C, 63.21; H, 7.81; N, 6.47.

Advantages of the Present Invention

1. A hitherto unknown series of highly functionalized artemisinin dimers has been synthesized which shows promising anti-cancer activity.

2. For the first time we introduced the Huisen 1,3-dipolar cycloaddition reaction for the synthesis of 1,2,3-triazole containing artemisinin derived 1,2,4-trioxane dimers.

3. All synthesized artemisinin derived dimers are showing higher anti-cancer activities against various cancer cell lines than their parent compound artemisinin.

We claim:

1. A compound of General Formula A

General Formula A

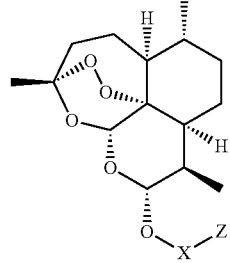

wherein X is

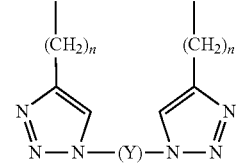

or

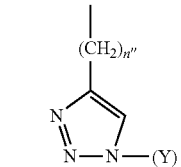

wherein n=0 to 2; n''=1 to 2;

Y is —(CH$_2$)$_{n'}$—, n'=3 to 9, or
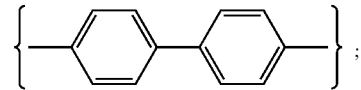
;
Y' is —(CH$_2$)$_{n'''}$—N$_3$, n'''=3 to 7; and
Z is
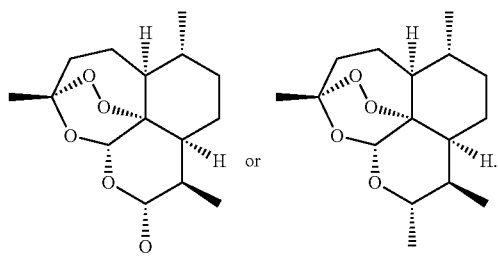
2. The compound of claim 1, selected from the group consisting of
Compound 9a
Compound 9b
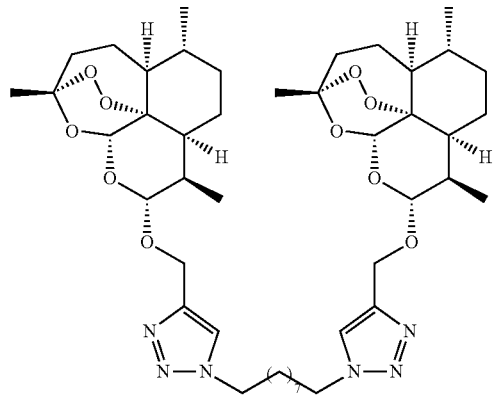
Compound 9c
Compound 10a
Compound 10b
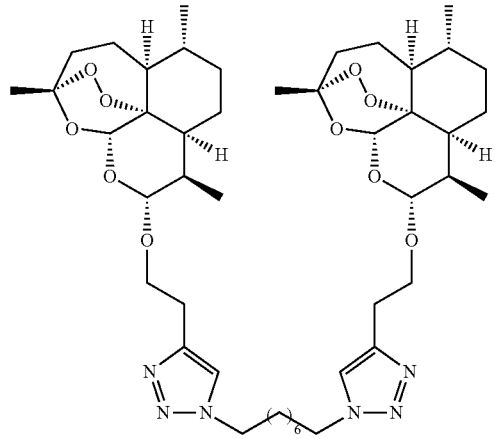
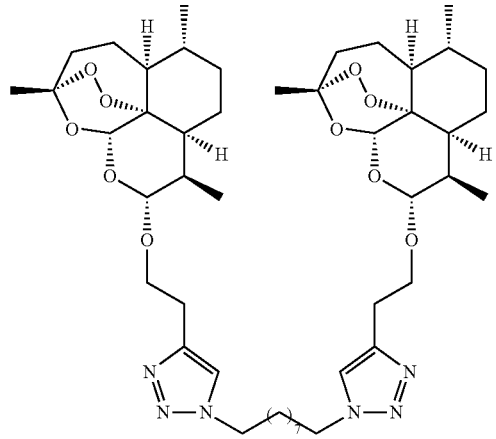

Compound 11

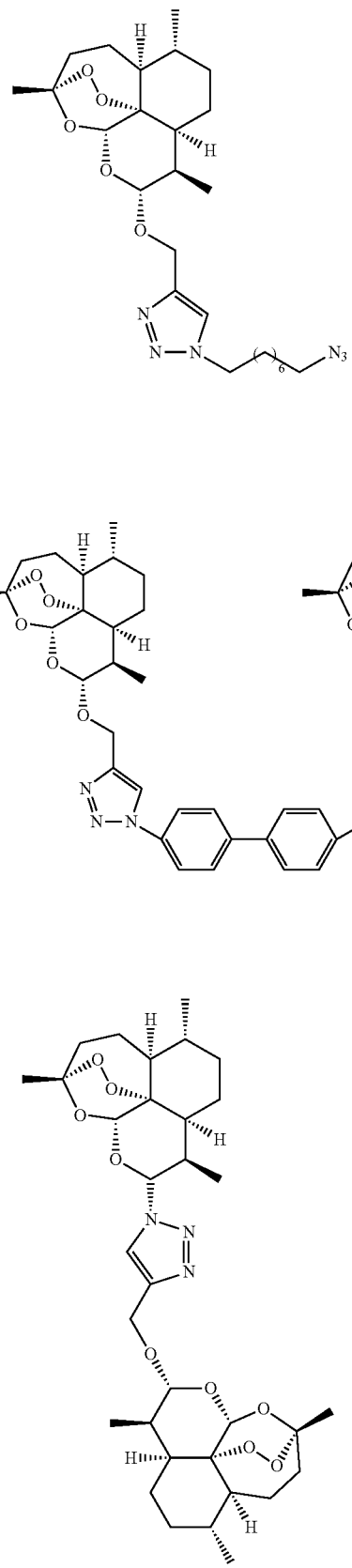

Compound 12

Compound 14

Compound 13

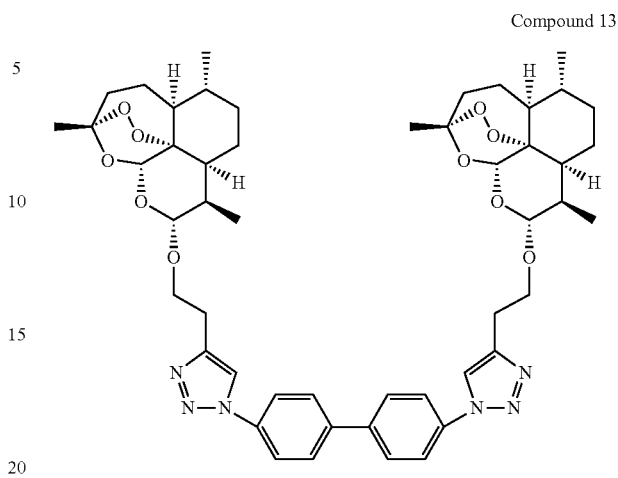

Compound 15

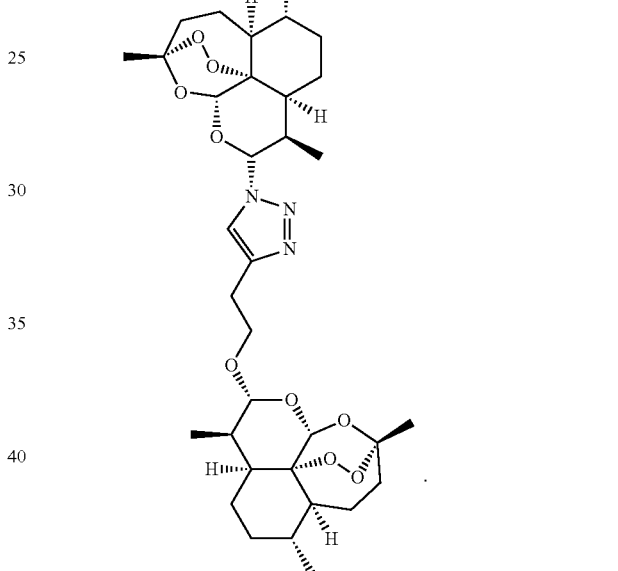

3. The compound of claim 1, wherein the compound is useful in the treatment of colon, lung, leukemia, and liver cancer.

4. The compound of claim 1, wherein the compound shows growth inhibition of colon HCT-15, Lung A549, leukemia, THP-1 and liver HEP-2 up to 97% at a concentration ranging $1\times10^{-5}$ to $5\times10^{-5}$ M.

5. The compound of claim 1, wherein the compound shows better growth inhibition of colon HCT-15, Lung A549, leukemia THP-1, and liver HEP-2 cells as compared to artemisinin.

6. A process for preparing the compound of claim 1, comprising the steps of:

(i) reacting dihydroartemisinin of Formula 5 with acetylenic alcohol in an organic solvent in presence of amberlyst-15 at a temperature in the range of 25-35° C. for a period ranging between 12-18 hrs to obtain the compound of Formula 7 or Formula 8;

Formula 5

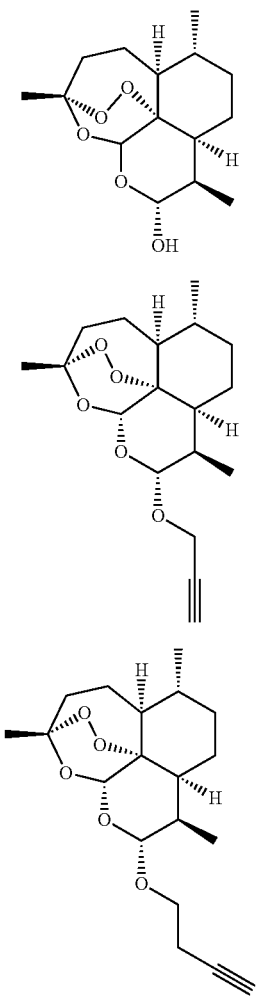

Formula 7

Formula 8

(ii) purifying the compound of Formula 7 or Formula 8 by a chromatography method using 5% ethyl acetate in hexane as a solvent; and
(iii) reacting the compound of Formula 7 or Formula 8 with an azido compounds selected from a group consisting of Compounds 2a-c, 4, and 6

Compound 2a

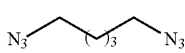

Compound 2b

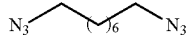

Compound 2c

Compound 4

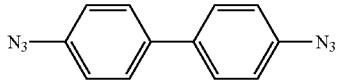

Compound 6

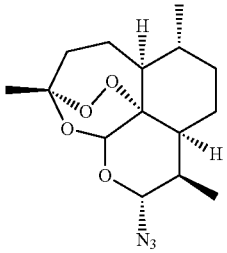

in presence of copper sulfate and sodium ascorbate in a solvent selected from a group consisting of dichloromethane and water (1:1), acetonitrile and water (1:1), chloroform and water (1:1), dimethylformamide and water (1:1) at a temperature ranging between 25-32° C., for a period ranging between 12 to 24 hour to obtain compound of General Formula A.

7. The process of claim 6, further comprising the step of (iv) purifying the compound of General Formula A using a chromatography method.

8. The process of claim 7, wherein the chromatography method used in step (iv) is selected from a group consisting of preparative thin layer chromatography, column chromatography, HPLC, and automated flash chromatography.

9. The process of claim 6, wherein the acetylenic alcohol is selected from a group consisting of 2-propyn-1-ol and 3-butyn-1-ol.

10. The process of claim 6, wherein the organic solvent in step (i) is selected from a group consisting of dichloromethane, chloroform, 1,2-dichloroethane, nitromethane, and acetonitrile.

11. The process of claim 7, wherein in the solvent used for the chromatographic method in step (iv) is selected from a group consisting of n-hexane, petroleum ether, iso-propanol, ethyl acetate, chloroform.

* * * * *